United States Patent
Hayasawa et al.

(10) Patent No.: US 6,815,419 B1
(45) Date of Patent: Nov. 9, 2004

(54) ANTIULCER AGENT

(75) Inventors: Hirotoshi Hayasawa, Zama (JP); Tomohiro Toida, Zama (JP); Yukiko Shimokawa, Zama (JP); Hiroshi Matsumoto, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/979,319

(22) PCT Filed: Jun. 16, 2000

(86) PCT No.: PCT/JP00/03965

§ 371 (c)(1),
(2), (4) Date: Nov. 21, 2001

(87) PCT Pub. No.: WO01/07077

PCT Pub. Date: Feb. 1, 2001

(30) Foreign Application Priority Data

Jul. 28, 1999 (JP) .......................................... 11-213782

(51) Int. Cl.⁷ ............................ A61K 38/17; C07K 2/00
(52) U.S. Cl. ......................................... 514/12; 530/365
(58) Field of Search ................................ 514/12, 2, 362, 514/925; 530/365; 426/35, 580, 583; 424/78.01

(56) References Cited

U.S. PATENT DOCUMENTS

| | | | | |
|---|---|---|---|---|
| 2,095,259 A | * | 10/1937 | Kober et al. | 514/54 |
| 2,520,615 A | * | 8/1950 | Strezynski | 530/366 |
| 2,585,225 A | * | 2/1952 | Carlson | 426/42 |
| 2,832,717 A | * | 4/1958 | Ferguson | 514/21 |
| 4,427,658 A | | 1/1984 | Maubois et al. | |
| 4,834,994 A | * | 5/1989 | Kuwata et al. | 426/271 |
| 5,725,861 A | | 3/1998 | Teichmann et al. | |
| 5,866,418 A | | 2/1999 | Ballard et al. | |
| 6,027,735 A | | 2/2000 | Teichmann et al. | |

FOREIGN PATENT DOCUMENTS

| | | |
|---|---|---|
| EP | 0 361 348 | 4/1990 |
| EP | 0 834 320 A1 | 4/1998 |
| JP | 56-32488 | 1/1981 |
| JP | 62-277327 | 12/1987 |
| JP | 1-268644 | 10/1989 |
| JP | 5-65295 | 3/1993 |
| JP | 5-246882 | 9/1993 |
| JP | 5-262793 | 10/1993 |
| JP | 5-271092 | 10/1993 |
| JP | 5-508542 | 12/1993 |
| JP | 7-203863 | 8/1995 |
| JP | 2000-63284 | 2/2000 |
| WO | 92/00994 | 1/1992 |

* cited by examiner

Primary Examiner—Robert A. Wax
(74) Attorney, Agent, or Firm—Nixon & Vanderhye P.C.

(57) ABSTRACT

The present invention provides antiulcer agents which can be orally administered while producing few side effects. These antiulcer agents contain α-lactalbumin as an active ingredient, preferably in an amount of at least 0.5 mg/g.

14 Claims, No Drawings

ANTIULCER AGENT

TECHNICAL FIELD

The present invention relates to an antiulcer agent. More specifically, the present invention relates to an antiulcer agent, including α-lactalbumin as an active ingredient, which produces no side effects.

BACKGROUND ART

An ulcer (a peptic ulcer) is tissue damage resulting from necrosis to a certain depth of skin or mucous membrane in the esophagus, stomach, or duodenum, which is directly caused by hydrochloric acid or pepsin in gastric juice induced by stress, alcohol, a nonsteroidal anti-inflammatory drug (NSAID) such as indomethacin, or the like.

Specific examples of the antiulcer agent used for treatment of ulcers include an antacid which can neutralize gastric acid, and an anticholinergic drug, an $H_2$ blocker, a proton pump inhibitor, and the like, which can suppress secretion of gastric acid.

Although specific examples of the antacids include sodium hydrogencarbonate, magnesium carbonate, aluminium hydroxide, and a mixture thereof, these have various problems. For example, they must be taken at frequent intervals because of the short duration of the action thereof, and the laxative action of the formulation is strong when it includes magnesium (Journal of Medicine, volume 27, page 2272, 1991).

Conventional anticholinergic drugs and $H_2$ blockers (such as cimetidine) are known to have various problems. For example, the acute toxicitic dose thereof is low, side effects are caused by the binding thereof to respective receptors somewhere other than lesions (for example, cimetidine is known to cause hematologic disorders, hepatic disorders, renal disorders, endocrine disorders, mental or nervous disorders, digestive disorders, and hypersensitivity), and interference with other drugs occurs (Journal of Medicine, volume 27, page 2272, 1991; and DRUGS in JAPAN edited by the Japan Pharmaceutical Information Center, Jiho Inc., page 517, 1993).

Conventional proton pump inhibitors also have problems such as the generation of carotenoids (Journal of Medicine, volume 27, page 2272, 1991).

In contrast, specific examples of the antiulcer agents containing a protein, or a peptide as an active ingredient, include secretin, somatostatin, calcitonin, urogastrone, and the like.

Moreover, specific examples of a formulation derived from whey include methanol extract of whey (Japanese Unexamined Patent Application, First Publication No. Sho 62-277327, which is referred hereinafter to as Prior Art 1), whey protein (Japanese Unexamined Patent Application, First Publication No. Hei 1-268644, which is referred hereinafter to as Prior Art 2), and whey protein degradation product which is hydrolyzed by an enzyme (Japanese Unexamined Patent Application, First Publication No. Sho 56-32488, which is referred hereinafter to as Prior Art 3).

The peptide formulation, such as secretin, somatostatin, or calcitonin has a problem in that it is required to be administered by injection, which is accompanied by pain, and continuous administration is difficult (Journal of Medicine, volume 27, page 2272, 1991).

Although urogastrone is a peptide formulation for oral administration, it has problems in that the amount of urogastrone which can be prepared is limited, and in that the cost required for preparing urogastrone is high because the raw material from which urogastrone is prepared by purification is pregnant mare urine. Moreover, administration of urogastrone tends to cause side effects such as thirst, nausea, discomfort in the gastric region, diarrhea, constipation, and/or the like (DRUGS in JAPAN edited by the Japan Pharmaceutical Information Center, Jiho Inc., page 517, 1993).

Moreover, the methanol extract of whey (Prior Art 1) has a problem in that it is difficult to be used as a food material, because methanol is unsuitable in view of food safety, and the antiulcer substances prepared from other wheys (Prior Arts 2 and 3) have a problem in that the antiulcer action thereof is insufficient.

Therefore, antiulcer agents having neither the problems described above nor the side effects described above are awaited.

α-lactalbumin is known to be a globular protein which accounts for approximately 25% (weight percent; the same units below unless specifically mentioned otherwise) of whey protein and has a molecular weight of approximately 14,100, and to play a part in a synthesis of lactose ("Comprehensive Encyclopedia of Milk" edited by Kunio Yamauchi and Kenkichi Yokoyama, Asakura-Shyoten Co., Ltd., page 35, 1992). Moreover, α-lactalbumin is known to have a gelation property and to be included in foods for masking effects or quality improvement, as well as in albumen substitutes, kneaded foods, or the like ("'94 The Present and the Future of Protein and Peptide Foods", Seed * Planning Co., Ltd., page 37, 1994).

However, α-lactalbumin is not known to have strong antiulcer action, and this is not disclosed in any literature.

As is obvious from the prior art described above, although antiulcer agents for oral administration having few side effects are awaited, substances have not yet been discovered having superior effects.

DISCLOSURE OF INVENTION

As a result of extensive research aimed at obtaining more effective antiulcer agents, the inventors of the present invention discovered that α-lactalbumin has antiulcer effects in vivo, and have thereby completed the present invention.

The present invention was made in view of the circumstances described above, and an object of the present invention is to provide an antiulcer agent, for oral administration, which produces few side effects.

The present invention, which can overcome the problems described above, is an antiulcer agent including α-lactalbumin as an active ingredient, wherein α-lactalbumin is preferably included in an amount of at least 0.5 mg per 1 g of the antiulcer agent. Moreover, α-lactalbumin is more preferably included as an active ingredient in an amount of 1 mg per 1 g of the antiulcer agent.

BEST MODE FOR CARRYING OUT THE INVENTION

In the following, the present invention will be explained in detail.

α-lactalbumin included as an active ingredient in an antiulcer agent according to the present invention can be prepared by the conventional ammonium sulfate precipitation method (for example, "New Edition of Modem Milk Engineering Handbook" written by Kinjirou Yukawa, Dairy Engineering Extension Association, pages 120 to 122, 1975). In order to obtain it more easily, commercially available α-lactalbumin (manufactured by Sigma Co., Ltd., for example) can be utilized.

Moreover, α-lactalbumin can also be prepared by the iron chloride method (Journal of Food Science, volume 50, pages 1531 to 1536, 1985), the ultrafiltration method (Japanese Unexamined Patent Application, First Publication No. Hei 5-268879), the ion exchange method (Japanese Patent No. 2916047), or the like.

As is obvious from experiments described below, α-lactalbumin has little toxicity, can be suitably used for oral administration, and can be processed by well known methods into tablets, capsules, troches, syrups, ampuled liquid medicines, granules, powders, or the like. Moreover, α-lactalbumin can be included in foods as an active ingredient to prepare foods having antiulcer properties as one embodiment of the antiulcer agents.

The antiulcer agents having various dosage forms described above can be respectively prepared by adding to α-lactalbumin a carrier which is pharmaceutically acceptable or can be used for foods. Specific examples of the carrier include aqueous solvents such as distilled water, purified water, saline solutions, and the like; excipients such as L-glutamine, magnesium silicate, crystallzed cellulose, wheat starch, rice starch, D-sorbitol, dextran, dextrin, corn starch, lactose, potato starch, powders of reduced maltose starch syrup, powders of cellulose, D-mannitol, aminoethyl sulfonate, fructose, xylitol, and the like; stabilizers such as sodium ascorbate, L-arginine, sodium arginate, benzoic acid, sodium edetate, glycerin, calcium gluconate, sodium chondroitin sulfate, β-cyclodextrin, L-cystine, ethyl parahydroxybenzoate, calcium pantothenate, potassium polyphosphate, sodium polyphosphate, methyl cellulose, and the like; pH buffer solutions containing respective pH regulators such as citric acid, sodium citrate, disodium citrate, sodium acetate, tartaric acid, sodium hydroxide, sodium hydrogencarbonate, calcium lactate, sodium hydrogenphosphate, disodium hydrogenphosphate, dipotassium hydrogenphosphate, potassium dihydrogenphosphate, succinic acid, sodium succinate, disodium succinate, or the like; antioxidants such as ascorbic acid, tocopherol, tocopherol acetate, natural vitamin E, sodium pyrosulfite, propyl gallate, and the like; lubricants such as sucrose fatty acid ester, lactose, calcium stearate, glycerine monostearate, and the like; emulsifiers such as carageenan, glycerine fatty acid ester, sodium stearate, soybean lecithin, propylene glycol, yolk lecithin, sodium lauryl sulfate, sorbitan fatty acid ester, propylene glycol fatty acid ester, and the like; edulcorants such as hydrangea tea, isomerized saccharide, liquid sugar syrup, syrup, saccharin, white sugar, honey, dextrose, starch syrup, and the like; and coatings such as a gelatin capsule, and the like.

Although the dose of α-lactalbumin included in the antiulcer agent as an active ingredient is determined in accordance with age, or the condition of a patient, or the like, it is required to be orally administered in an amount of at least 10 mg per 1 kg of body weight, so as to exhibit antiulcer effects, as is obvious from the experiments described below.

In the antiulcer agent according to the present invention, the content of α-lactalbumin included as an active ingredient for obtaining antiulcer effects is required to be at least 0.5 mg per 1 g of the antiulcer agent. Moreover, α-lactalbumin is more preferably included as an active ingredient in an amount of at least 1 mg per 1 g of the antiulcer agent.

Although the antiulcer agents according to the present invention have curative or preventive effects on lesions in the gastrointestinal mucous membrane, the degree of the effects depends on the causes of the ulcers, as is obvious from the experiments described below. For example, the antiulcer agent can exhibit superior curative or preventive effects against stress-induced ulcers caused by stress, or alcohol-induced ulcers caused by alcohol, in comparison with ulcers induced by a nonsteroidal anti-inflammatory drug (NSAID) such as indomethacin.

In the following, the present invention will be explained in detail by experiments.

EXPERIMENT 1

The purpose of this experiment is to investigate antiulcer effects of the present invention in comparison with the prior art.

(1) Test Animals

Male Wistar rats weighing 230 to 270 g, 11 weeks old, (purchased from Japan SLC CO., Ltd.) were randomly classified into five groups (each consisting of ten rats).

(2) Test Agents

Test agent 1: Distilled water for injection (blank test).
Test agent 2: An antiulcer agent in which an antiulcer substance prepared in a manner identical to Example 1 described in Prior Art 1 is dissolved in distilled water to a concentration of 1 mg/ml.
Test agent 3: An antiulcer agent in which a commercially available whey protein (manufactured by Mirai Inc.) described in Prior Art 2 is dissolved in distilled water to a concentration of 1 mg/ml.
Test agent 4: An antiulcer agent in which a peptide hydrolysate prepared in a manner identical to Examples 2 and 3 described in Prior Art 3 and described in Example 4 of the present invention is dissolved in distilled water to a concentration of 1 mg/ml.
Test agent 5: An antiulcer agent of the present invention, in which a commercially available α-lactalbumin (manufactured by Sigma Co., Ltd.) is dissolved in distilled water to a concentration of 1 mg/ml.

(3) Test Method

The experiment was carried out according to the method disclosed by Robert et al. (Gastroenterology, volume 77, pages 433 to 443, 1979). That is, rats were fasted for 24 hours and were orally administered with each test agent at a dose of 10 mg/kg of an active ingredient in body weight. Test agent 1 for a blank test was orally administered to the rats in an amount of 10 ml/kg body weight. After 30 minutes, hydrochloric acid and ethanol solution [hydrochloric acid and ethanol solution (M=mol/dm$^3$) prepared by mixing 500 mM of hydrogen chloride (HCl) solution and 75% ethanol solution at a volume ratio of 1.4)] was orally administered to the rats at a dose of 5 ml/kg body weight.

After 1 hour, the rats were killed by ether inhalation, the stomach of each rat was taken out to the body surface, the pyloric part of the stomach was ligated, and then the stomach was removed. Then, 10 ml of 2% formalin solution was injected into the stomach from the cardiac part thereof, and the stomach was subsequently immersed in the formalin solution for 10 minutes for fixation. Then, the curvatura ventriculi major of the stomach fixed by formalin was cut to open, and the degree of ulcers was measured by the following method.

That is, the total area of injured portions on the mucous membrane of each rat was measured, and then the degree of lesions on the mucous membrane of each rat (score) was classified into six grades as shown in Table 1 in accordance with the total area of the injured portion. Moreover, the cumulative degree, which is the sum total of the degree of lesions on mucous membranes of ten rats in each group, was calculated as an index which shows the degree of ulcers in each group.

TABLE 1

| Degree of lesions on mucous membrane (score) | Total area of injured portions on mucous membrane (mm²) |
| --- | --- |
| 0 | 0 |
| 1 | 1~20 |
| 2 | 21~40 |
| 3 | 41~60 |
| 4 | 61~80 |
| 5 | 81~100 |
| 6 | over 100 |

(4) Test Results

Results of this experiment are shown in Table 2. As is clear from Table 2, Test agent 5 of the present invention has superior antiulcer effects in comparison with Test agent 2 to 4, each of which includes a conventional antiulcer agent.

Moreover, although other types of α-lactalbumin were also tested in the same way, similar results were obtained.

TABLE 2

| Number of test agent | Cumulative degree of lesions on mucous membrane |
| --- | --- |
| 1 | 60 |
| 2 | 35 |
| 3 | 53 |
| 4 | 46 |
| 5 | 7 |

EXPERIMENT 2

This experiment was carried out in order to examine the acute toxicity of α-lactalbumin (1) Test Animals Male and Female CD (SD) rats, 6 weeks old, purchased from Japan SLC CO., Ltd.) were respectively and randomly classified into three groups (each consisting of five rats) to be used for this experiment.

(2) Test Method

Commercially available α-lactalbumin (manufactured by Sigma Co., Ltd.) was dissolved in water for injection (manufactured by Otsuka Pharmaceutical Co., Ltd.) to each of a concentration of 100 mg/ml and 200 mg/ml, which were respectively and orally administered in an amount of 1 ml per 100 g of body weight (at each dose of 1000 mg and 2000 mg per 1 kg of rat body weight) to each rat of each group by single oral instillation by means of a metal probe with a rounded tip, in order to examine the acute toxicity. As a blank test, only water for injection (manufactured by Otsuka Pharmaceutical Co., Ltd.) was administered in the same way to each rat of both groups of males and females.

(3) Test Results

Results of this experiment are shown in Table 3. As is clear from Table 3, no deaths occurred in groups administered with α-lactalbumin at a dose of 1000 mg/kg in body weight or 2000 mg/kg in body weight as well as in the blank test (0 mg/kg). Therefore, it was determined that the $LD_{50}$ of α-lactalbumin was no less than 2000 mg/kg body weight, indicating that the toxicity of α-lactalbumin was extremely low.

Moreover, although other types of α-lactalbumin were also examined in the same way, similar results were obtained.

TABLE 3

| Dose | Number of deaths/Total number | |
| --- | --- | --- |
| (mg/kg) | Male | Female |
| 0 | 0/5 | 0/5 |
| 1000 | 0/5 | 0/5 |
| 2000 | 0/5 | 0/5 |

EXPERIMENT 3

This experiment was carried out in order to examine the effective dose of α-lactalbumin.

(4) Test Animals

Male Wistar rats weighing 230 to 270 g, being 11 weeks old, (purchased from Japan SLC CO., Ltd.) were randomly classified into four groups (each consisting of ten rats).

(2) Test Agents

As a test agent (an antiulcer agent including α-lactalbumin of the present invention as an active ingredient), commercially available α-lactalbumin (manufactured by Sigma Co., Ltd.) was dissolved in distilled water to a concentration of 1 mg/ml. As a test agent for a blank test, distilled water was used.

(3) Test Method

This experiment was carried out in a manner identical to Example 1, except that α-lactalbumin included in the test agents as an active ingredient was respectively orally administered at a dose of 0 mg/kg body weight (blank test), 1 mg/kg body weight, 10 mg/kg body weight, or 100 mg/kg body weight.

(4) Test Results

Results of this experiment are shown in Table 4. As is clear from Table 4, α-lactalbumin shows significant antiulcer effects by oral administration at a dose of no less than 10 mg per 1 kg of body weight. From these results, it was determined that an effective dose for oral administration of α-lactalbumin was at least 10 mg per 1 kg of body weight.

Moreover, although other types of α-lactalbumin were also examined in the same way, similar results were obtained.

TABLE 4

| Dose of active ingredient (mg/kg) | Cumulative degree of lesions on mucous membrane |
| --- | --- |
| 0 | 60 |
| 1 | 47 |
| 10 | 7 |
| 100 | 3 |

EXPERIMENT 4

This experiment was carried out for the purpose of examining the required concentration of α-lactalbumin in an antiulcer agent of the present invention.

(1) Test Animals

Male Wistar rats weighing 230 to 270 g, 11 weeks old, (purchased from Japan SLC CO., Ltd.) were randomly classified into six groups (each consisting of ten rats).

(2) Test Agents

As test agents (antiulcer agents including α-lactalbumin of the present invention as an active ingredient), commercially available α-lactalbumin (manufactured by Sigma Co., Ltd.) was dissolved in distilled water to each concentration (content) of 0.25 mg/ml, 0.5 mg/ml, 1 mg/ml, and 5 mg/ml. As a test agent for a blank test, distilled water was used.

(3) Test Method

This experiment was carried out in a manner identical to Example 1, except that α-lactalbumin included as an active ingredient in each test agent was respectively orally administered at a dose of 10 mg/kg body weight. The dose for the blank test was 0 mg/kg body weight.

(4) Test Results

Results of this experiment are shown in Table 5. As is clear from Table 5, when the dose was fixed to the minimum effective dose as shown in Experiment 3 described above (in the ratio of 10 mg to 1 kg of body weight) and the concentration of α-lactalbumin is set to 0.25 mg/ml, 0.5 mg/ml, 1 mg/ml, or 5 mg/ml, test agents including α-lactalbumin at a concentration of no less than 0.5 mg/ml (0.5 mg/g when the specific gravity of distilled water is 1) show antiulcer effects. Moreover, test agents including α-lactalbumin at a concentration of no less than 1 mg/ml (1 mg/g when the specific gravity of distilled water is 1) show significant antiulcer effects. From these test results, it was identified that the concentration of α-lactalbumin included in an antiulcer agent as an active ingredient is required to be no less than 05 mg per 1 g.

Moreover, although other types of α-lactalbumin were also examined in the same way, similar results were obtained.

TABLE 5

| Concentration (mg/ml) | Dose of active ingredient (mg/kg) | Cumulative degree of lesions on mucous membrane |
|---|---|---|
| 0 | 0 | 60 |
| 0.25 | 10 | 30 |
| 0.5 | 10 | 13 |
| 1 | 10 | 7 |
| 5 | 10 | 5 |
| 10 | 10 | 5 |

EXPERIMENT 5

This experiment was carried out for the purpose of examining whether the antiulcer effects of an antiulcer agent according to the present invention depend on the cause of the ulcers.

(1) Test Animals

Male Wistar rats weighing 230 to 270 g, 11 weeks old, (purchased from Japan SLC CO., Ltd.) were randomly classified into six groups (each consisting of ten rats).

(2) Test Agents

As test agents (antiulcer agents including α-lactalbumin of the present invention as an active ingredient), commercially available α-lactalbumin (manufactured by Sigma Co., Ltd.) was dissolved in distilled water to a concentration of 1 mg/ml to be used. As a test agent for a blank test, distilled water was used.

(3) Test Method (a) Test Method 1 (Method for Induction of Alcohol-Induced Ulcers)

This experiment was carried out according to the method disclosed by Robert et al. (Gastroenterology, volume 77, pages 433 to 443, 1979) in a manner similar to Example 1. That is, rats fasted for 24 hours were orally administered with each test agent at a dose of 10 mg/kg of an active ingredient in body weight (test group number 1). The test agent for a blank test was orally administered to rats in an amount of 10 ml/kg in body weight (test group number 2). After 30 minutes, hydrochloric acid and ethanol solution [hydrochloric acid and ethanol solution (M=mol/dm$^3$) prepared by mixing 500 mM of hydrogen chloride (HCl) solution and 75% ethanol solution at a volume ratio of 1:4)] was orally administered to the rats at a dose of 5 ml/kg body weight.

After 7 hours, the rats were killed by ether inhalation, the stomach of each rat was taken out to the body surface, the pyloric part of the stomach was ligated, and then the stomach was removed. Then, 10 ml of 2% formalin solution was injected into the stomach from cardiac part thereof, and the stomach was subsequently immersed in the formalin solution for 10 minutes for fixation. Then, the curvatura ventriculi major of the stomach fixed by formalin was cut to open, and the degree of ulcers was measured in a manner identical to Example 1.

(b) Test Method 2 (Method for Induction of Stress-induced Ulcers)

This experiment was carried out in a manner identical to Method 1 described above, except that ulcers were induced according to the method described by Takagi and Okabe (Japanese Journal of Pharmacology, volume 18, pages 9 to 18, 1968). That is, rats fasted for 24 hours were orally administered with each test agent including at a dose of 10 mg/kg of an active ingredient in body weight (test group number 3). The test agent for a blank test was orally administered to rats in an amount of 10 ml/kg body weight (test group number 4). After 30 minutes, each rat was held in a stainless steel restrictive cage, and was left in a water tank at 23° C., standing and submerging to the depth of the bottom of the breast xiphoid process of the rat.

After 7 hours, each rat was pulled up from the water tank, and the degree of ulcers was measured in a manner identical to Method 1 described above.

(c) Test Method 3 (Method for Induction of Ulcers Caused by a Nonsteroidal Anti-inflammatory Drug)

This experiment was carried out in a manner identical to Method 1 described above, except that ulcers were induced in accordance with the method of Okabe, et al. (Japanese Journal of Pharmacology, volume 29, pages 670 to 673, 1968). That is, rats fasted for 24 hours were orally administered with the each test agent at a dose of 10 mg/kg of an active ingredient in body weight (test group number 5). The test agent for a blank test was orally administered to each rat in an amount of 10 ml/kg body weight (test group number 6). After 30 minutes, indomethacin at a dose of 30 mg/kg body weight, which is a representative nonsteroidal anti-inflammatory drug, was orally administered.

After 7 hours, the degree of ulcers was measured in a manner identical to Method 1 described above.

(4) Test Results

Results of this experiment are shown in Table 6. As is clear from Table 6, antiulcer actions of the antiulcer agent according to the present invention are recognized to be different in accordance with the causes of induction of ulcers, and antiulcer action on stress-induced ulcers caused by stress (test group number 3) turned out to be superior to that on ulcers caused by indomethacin which is a representative nonsteroidal anti-inflammatory drug (test group number 5).

Moreover, it is turned out that the antiulcer agent according to the present invention has a greater superior antiulcer action on alcohol-induced ulcers caused by alcohol (test group number 1) in comparison with antiulcer actions on the ulcers caused by indomethacin (test group number 5), and the antiulcer actions on alcohol-induced ulcers caused by alcohol (test group number 1) is superior to the antiulcer actions on stress-induced ulcers (test group number 3).

Results of blank tests in Methods 1 to 3 (test group numbers 2, 4, and 6), in each of which the cumulative degree of lesions on mucous membranes is the same value, show that antiulcer effects obtained in Methods 1 to 3 can be compared with one another.

Moreover, although other types of α-lactalbumin were also examined in the same way, similar results were obtained.

TABLE 6

| Test group number | Cumulative degree of lesions on mucous membrane |
|---|---|
| 1 | 6 |
| 2 | 50 |
| 3 | 12 |
| 4 | 50 |
| 5 | 23 |
| 6 | 50 |

In the following, although the present invention will be explained in more detail by way of Examples, the present invention is not limited to the following Examples.

EXAMPLES

Example 1

Tablets of an antiulcer agent including following compositions were prepared in accordance with the following method.

| | |
|---|---|
| Lactose (manufactured by Megre Co., Ltd.) | 18.8 (%) |
| Corn starch (manufactured by Ohoji Corn Starch Co., Ltd.) | 67.9 |
| Magnesium stearate (manufactured by Wako Pure Chemicals Co., Ltd.) | 1.4 |
| Calcium carboxymethylcellulose (manufactured by Dai-ichi Kogyo Seiyaku Co., Ltd.) | 9.4 |
| α-lactalbumin (manufactured by Sigma Co., Ltd.) | 2.5 |

A mixture including α-lactalbumin, lactose, corn starch, and calcium carboxymethylcellulose was uniformly kneaded with suitably adding sterilized purified water, and was dried at 50° C. for 3 hours to obtain a dry substance. Then, magnesium stearate was added into the dry substance followed by mixing and forming of tablets in accordance with a conventional procedure using a machine for making tablets.

Example 2

An antiulcer syrup including the following components was prepared in accordance with a conventional procedure.

| | |
|---|---|
| Calcium carboxymethylcellulose (manufactured by Dai-ichi Kogyo Seiyaku Co., Ltd.) | 0.20 (%) |
| Sodium citrate (manufactured by Wako Pure Chemicals Co., Ltd.) | 0.18 |
| Citric acid (manufactured by Wako Pure Chemicals Co., Ltd.) | 0.22 |
| Fructose glucose liquid sugar syrup (manufactured by Otsuka Pharmaceutical Co., Ltd.) | 19.83 |
| Purified water (manufactured by Otsuka Pharmaceutical Co., Ltd.) | 78.57 |
| α-lactalbumin (manufactured by Sigma Co., Ltd.) | 1.00 |

Example 3

An antiulcer powdered medicine including the following components was prepared in accordance with the following procedure.

| | |
|---|---|
| Corn starch (manufactured by Ohoji Corn Starch Co., Ltd.) | 57.5 (%) |
| Crystallized cellulose (manufactured by Wako Pure Chemicals Co., Ltd.) | 37.5 |
| α-lactalbumin (manufactured by Sigma Co., Ltd.) | 5.0 |

Materials described above were mixed uniformly and were prepared into powers in accordance with a conventional procedure.

INDUSTRIAL APPLICABILITY

As described above in detail, the present invention relates to antiulcer agents including α-lactalbumin as an active ingredient, and can achieve the following effects.

(1) Because the antiulcer agents produce few side effects, they can be administered for a long time.

(2) Because α-lactalbumin has heat-resisting properties, and has water-soluble properties which causes stability in a solution, it is stable as a drug.

(3) Because the antiulcer agents can be orally administered, they can be easily administered for general purposes in comparison with injection.

(4) Because α-lactalbumin can be prepared from relatively inexpensive raw materials such as milk or the like, it can be prepared on a large scale.

What is claimed is:

1. A method for treatment of ulcers, comprising the step of administering an antiulcer agent consisting of α-lactalbumin as the sole antiulcer agent to a subject in need thereof.

2. A method of treating ulcers comprising administering at least 10 mg per kilogram of body weight per dose of α-lactalbumin as the sole active ingredient to a subject in need thereof.

3. A method of treating ulcers comprising administering a composition consisting of at least 10 mg per kilogram of body weight per dose of α-lactalbumin as the sole active ingredient together with a pharmaceutically accepted carrier to a subject in need thereof.

4. A method of treating ulcers according to claim 2, wherein the dose is at least 100 mg per kilogram of body weight.

5. The method of treating ulcers according to claim 3, wherein the composition contains at least 1 mg of α-lactalbumin per 1 g of composition.

6. The method of treating ulcers according to claim 3, wherein the composition contains at least 5 mg of α-lactalbumin per 1 g of composition.

7. The method of treating ulcers according to claim 3, wherein the composition contains at least 10 mg of α-lactalbumin per 1 g of composition.

8. The method of treating ulcers according to claim 3, wherein the composition contains at least 25 mg of α-lactalbumin per 1 g of composition.

9. The method of treating ulcers according to claim 3, wherein the composition contains at least 50 mg of α-lactalbumin per 1 g of composition.

10. The method of treating ulcers according to claim 3, wherein, in addition to α-lactalbumin, the composition includes at least one or more of an aqueous solvent, an excipient, a stabilizer, a pH buffer solution containing pH buffers, an antioxidant, a lubricant, an emulsifier, an edulcorant or a coating.

11. The method of treating ulcers according to claim 3, wherein the composition has a form of a tablet, capsule, troche, syrup, ampuled liquid medicine, granule or a powder.

12. A method of treating ulcers according to claim 2 wherein the ulcers are stress-induced ulcers, alcohol-induced ulcers, or ulcers caused by a nonsteroidal anti-inflammatory drug.

13. A method of treating ulcers according to claim 3 wherein the ulcers are stress-induced ulcers, alcohol-induced ulcers, or ulcers caused by a nonsteroidal anti-inflammatory drug.

14. A method of treating ulcers according to claim 4 wherein the ulcers are stress-induced ulcers, alcohol-induced ulcers, or ulcers caused by a nonsteroidal anti-inflammatory drug.

\* \* \* \* \*